United States Patent [19]

Whitbourne

[11] Patent Number: 5,001,009

[45] Date of Patent: Mar. 19, 1991

[54] LUBRICIOUS HYDROPHILIC COMPOSITE COATED ON SUBSTRATES

[75] Inventor: Richard J. Whitbourne, Fairport, N.Y.

[73] Assignee: Sterilization Technical Services, Inc., Rush, N.Y.

[21] Appl. No.: 92,077

[22] Filed: Sep. 2, 1987

[51] Int. Cl.$^5$ .............................................. B32B 27/36
[52] U.S. Cl. .................................... 428/412; 428/421; 428/423.3; 428/423.5; 428/423.7; 428/424.4; 428/424.6; 428/424.8; 428/425.5; 428/425.6; 428/425.8; 428/430; 428/435; 428/441; 428/442; 428/451; 428/458; 428/461; 428/480; 428/483; 428/463; 428/474.9; 428/475.8; 428/476.1; 428/476.3; 428/476.9; 428/516; 428/517; 525/303
[58] Field of Search ...................... 428/412, 421, 423.3, 428/480, 423.5, 423.7, 424.6, 424.8, 424.4, 425.5, 425.6, 425.8, 480, 435, 441, 442, 451, 458, 461, 462, 463, 483, 474.9, 516, 475.8, 476.1, 517, 476.3, 476.9; 525/303

[56] References Cited

U.S. PATENT DOCUMENTS

| | | | |
|---|---|---|---|
| 3,914,341 | 10/1975 | Kliment et al. | 525/303 |
| 3,939,049 | 2/1976 | Ratner | 525/303 |
| 3,975,350 | 8/1976 | Hudgin et al. | 524/111 |
| 4,038,264 | 7/1977 | Rostoker et al. | 525/303 |
| 4,156,066 | 5/1979 | Gould . | |
| 4,156,067 | 5/1979 | Gould . | |
| 4,255,550 | 5/1981 | Gould . | |
| 4,496,535 | 1/1985 | Gould et al. . | |

Primary Examiner—P. C. Sluby
Attorney, Agent, or Firm—Kenyon & Kenyon

[57] ABSTRACT

The lubricious hydrophilic coatings of the invention include a hydrophilic polyolefin such as polyvinyl-pyrrolidone and a water-insoluble stabilizing polymer such as a cellulose ester. The coatings may also include an adherent polymer and a plasticizing agent. The coatings are significantly more lubricious when wet than when dry, are adherent to a variety of substrates, and are resistant to removal by wet abrasion. The coating method of the invention involves preparing a solution of the stabilizing polymer and a solution of the hydrophilic polyolefin, and coating the substrate first in one then the other. Alternatively, both the insolubilizing and hydrophilic polymers may be dissolved in a single solvent system and applied to the substrate in a single step. The solutions of the invention are stable, non-reactive, and non-hazardous. The coatings of the invention may be applied to biomedical devices and implants such as catheters, condoms, and nasogastric and endotracheal tubes.

18 Claims, No Drawings

LUBRICIOUS HYDROPHILIC COMPOSITE COATED ON SUBSTRATES

BACKGROUND OF THE INVENTION

This invention relates to hydrophilic, lubricant coatings that make biomedical devices slippery when wet. The method and coating of the invention may be employed to reduce the coefficient of friction of catheters, condoms, contact lenses, peristaltic pump chambers, arteriovenous shunts, gastroenteric feed tubes and endotracheal tubes, or other implants of metal or polymer substrate.

Known lubricious coatings that may be applied to biomedical devices include coatings of polyvinylpyrrolidone (PVP), polyurethane, acrylic polyester, vinyl resin, fluorocarbons, silicone, rubber, or combinations of these substances. For example, Micklus et al., U.S. Pat. No. 4,100,309 and U.S. Pat. No. 4,119,094 relate to a hydrophilic coating of PVP-polyurethane interpolymer formed with polyisocyanate. Ratner et al., U.S. Pat. No. 3,939,049, relates to a method of grafting hydrogels to polymeric substrates using radiation Hudgin et al., U.S. Pat. No. 3,975,350, relates to hydrophilic polyurethane polymers. Stoy et al., U.S. Pat. No. 3,987,497, relates to a tendon prosthesis with hydrogel coating.

These known hydrogel coatings have disadvantages: They may have an insufficiently low coefficient of friction, they may lack permanence (such as silicone or fluorocarbons), they may be slippery when dry as well as wet, making handling difficult, or (such as the Micklus et al. coatings) they may require the use of hazardous solvents to prepare them and contain unstable, reactive materials, so that separate and new solutions must be prepared daily or more frequently.

Furthermore, in the PVP-polyurethane coatings, little control can be exerted over the degree of lubricity and resistance to wet abrasion of the coatings, and such coatings are often unstable.

In order to solve these problems a hydrophilic lubricant coating was needed which, when wetted, has sufficient lubricity to be useful for biomedical devices such as implants, which adheres to a wide variety of substrates and resists wet abrasion, and which can be prepared from chemically stable and biocompatible solvents.

SUMMARY OF THE INVENTION

The hydrophilic coating of the invention comprises a hydrophilic polymer and a stabilizing polymer in a layer bonded to the surface of the device. The hydrophilic polymer is a polyolefin such as a vinyl polymer having polar pendant groups, a polyacrylate or methacrylate having hydrophilic esterifying groups, a polyether, a polyethylene glycol, or other polyolefin with hydrophilic characteristics. The hydrophilic polymer is preferably PVP or PVP/vinyl acetate. The stabilizing polymer is a water-insoluble polymer that does not significantly react with the hydrophilic polymer in solution, and is preferably cellulose ester, a copolymer of polymethyl vinyl ether and maleic anhydride, or nylon. The cellulose esters are most preferred. They include ethyl cellulose, hydroxyethyl cellulose, cellulose nitrate, cellulose acetate, cellulose acetate butyrate, and cellulose acetate proprionate.

Preferably, the coating has an inner layer where the stabilizing polymer is concentrated and an outer layer where the hydrophilic polymer is concentrated.

The coating may also contain an adherent polymer such as polyurethane, polyester, styrene polybutadiene, acrylic resin, polyvinylidene chloride, polycarbonate, and polyvinyl chloride, preferably in the inner layer to promote adhesion to the surface of the device.

A most preferred outer layer composition uses PVP of high molecular weight (e.g. 120,000–360,000), and a most preferred inner layer composition includes PVP with low molecular weight (as low as 15,000).

The inventive coating may be applied to a polymer surface such as polyurethane, polyvinyl chloride, polyacrylate, polycarbonate, polystyrene, polyester resin, polybutadiene-styrene copolymers, nylon, polypropylene, polybutylene, teflon, silicon, and polyvinyl acetal. The coating of the invention can also be applied to glass or metals such as stainless steel. The coating components can be selected to produce a coating with desired properties on these surfaces.

The method of preparing the coatings of the invention employs stable, non-toxic solutions which may be stored and handled with minimal precautions. The method of applying the coating of the invention comprises preparing a first organic solution of from about 0.01% to about 30% weight to volume of stabilizing polymer, preferably from about 0.2% to about 10%, applying the solution to a substrate surface, and evaporating the solvent, preferably at elevated temperature, then preparing a second solution of from about 0.01% to about 30% weight to volume hydrophilic polymer, preferably from about 0.5% to about 20%, applying it to the treated surface substrate and evaporating it.

The stabilizing polymer solution may also contain from about 0.01% to about 10% of hydrophilic polymer, preferably from about 0.1% to about 5%. The hydrophilic polymer solution may also contain from about 0.01% to about 20% of stabilizing polymer, preferably from about 0.1% to about 10%. Alternatively, the stabilizing polymer and hydrophilic polymer can be prepared in a single solution and applied in a single step.

The surface of the device may be pre-treated to promote adhesion of the coating. The solutions may also contain from about 0.1% to about 15% of an adherent polymer, preferably from about 1.0% to about 8.0% weight to volume to promote the bond between substrate and coating.

A plasticizing agent may be included with the stabilizing polymers, in a concentration of from about 0.01% to about 10%, preferably from about 0.1% to about 5.0%, weight to volume. The plasticizing agent may be camphor, castor oil, dioctyl phthalate, acetyl tributyl citrate, dibutyl sebacate, sebacic acid, alkyl resin, dibutylphthalate, polyvinylbutyral or other commonly known plasticizers, singly or in combination. The plasticizing agent is preferably included in the solution of stabilizing polymer. The inventive coating may include a plasticizer to enhance the flexibility of the coating, which may be preferable when the object to be coated is likely to bend during use. Also, the inclusion of a plasticizer is preferred when the stabilizing polymer is nitrocellulose, because the plasticizer reduces the tendency of nitrocellulose to oxidize rapidly or even combust when it is dried in a pure form.

Solvents for the stabilizing and adherent polymer include organic solvents such as ketones, esters, toluene, lactones, dimethylformamide, halogenated solvents, tetrahydrofuran, dioxane, amines, glycol butyl ether, alkyl acetates, acetonitrile, and other commonly known organic solvents. The less toxic solvents are preferred. The inclusion of small amounts of hydroxyl groups such as alcohols and moisture in the solvent does not have a significant detrimental effect on the coating and method of the invention.

Solvents for the hydrophilic polymer include most of the above as well as alcohols, acetic acid, and like solvents. A solvent system may be selected that is capable of dissolving all the constituents of the coating in a uniform solution, can act as a co-solvent in the layer, and is non-toxic. If desirable, a solvent may be selected that interacts with the particular substrate surface to promote adhesion.

The solutions may be applied by dipping the object to be coated into a vessel containing the solution, or the solutions may be poured, pumped, brushed or sprayed onto the object.

DETAILED DESCRIPTION OF THE INVENTION

The hydrophilic coatings of this invention are highly lubricious when wetted with an aqueous solution such as body fluid, or a lower alcohol such as ethanol or methanol, yet they are substantially less slippery when dry. Thus, an implant coated according to the invention remains non-slippery for ease of handling and preparation, but becomes lubricious when implanted, so as to protect the patient. The lubricity of the coating can be adjusted within a desirable range.

A coating according to the invention may be applied to the surface of a biomedical or other device with sufficient thickness and permanence to retain the coating's desirable qualities throughout the useful life of the coated device. The coatings of the invention are non-reactive with living tissue and are non-thrombogenic in blood.

The coating of the invention has beneficial characteristics for use on the surfaces of devices such as biomedical implants. The coating is hydrophilic, absorbing water and swelling in an aqueous environment to become a hydrogel. The coating has lubricant properties, and is significantly more slippery when wet than when dry. The coating is thin, on the order of magnitude of one thousandth of an inch. The coating is coherent and resistant to removal by wet abrasion, and it is adherent to a wide variety of substrates. The coating employs biocompatible substances that are neither toxic nor irritant. The functional characteristics of the coating may be varied as appropriate for many different applications.

The method of the invention is beneficial because the components can be varied to control lubricity, swelling, flexibility, and resistance to removal by wet abrasion. These characteristics of the coating can thus be adjusted for various substrates and applications. The method is also beneficial because the solutions of the invention have good shelf stability and remain substantially free of precipitate for periods in the range of months or years, so that various mixtures of the solutions for coatings may be prepared at one time and used to coat substrates later. Alternatively, the hydrophilic and stabilizing polymers, and if desired, a plasticizing agent and an adherent polymer, may even be prepared in a single solution. Furthermore, since the invention does not require the use of chlorinated solvents or other acute toxics, fewer precautions are necessary to protect workers from health hazards.

Without intending to limit the invention to its mode of operation, apparently the stabilizing polymers of the invention, particularly modified cellulose polymers, are able to make hydrophilic polymers, such as PVP and PVP-vinyl acetate copolymers, stable and insoluble in water and lower alcohols. The resulting combination, when applied to a substrate, produces a coating that is a stable layer or layers that are bonded to a substrate surface, is not slippery when dry but is desirably lubricious when wet, and is resistant to removal by conditions of wet abrasion. The coating layer bonds to an impervious surface such as stainless steel or glass. It also bonds to polymer surfaces where the surface interacts with the components of the coating.

It is possible to control the degree of stability, wet lubricity, insolubility, flexibility, and adhesion of the coating by varying the weight to volume percentages of the components in the coating solutions. Substantially all of the polymers and plasticizers deposited from solutions onto the surface of the object being coated remain in the layer of the coating after the solvents are evaporated. Also, the duration and temperature of the evaporating step may be selected to achieve stability of the coating layer and to achieve a bond between the surface being coated and the coating layer.

The hydrophilic polymers of the coatings are generally PVP of higher molecular weight, 120,000–360,000. PVP of lower molecular weight, as low as 15,000, can be used in the underlayer or base coating next to the substrate without deterioration of performance. Some or all of the PVP can be replaced with PVP-vinylacetate copolymer in the one-coat embodiment, or in either layer of the two-coat embodiment.

It has been found that the most preferred stabilizing polymer is water-insoluble cellulose polymer. Alternatives to modified cellulose polymers, such as polymethylvinylether/maleic anhydride and nylon may be used instead of or in addition to the modified cellulose polymers but these are more difficult to work with, and tend to produce coatings with less long-term wet abrasion resistance than coatings prepared without them. When the stabilizing polymer is nitrocellulose, it is preferable to include a plasticizing agent.

When tested by subjective methods the coatings of the invention, when wet, are more slippery than wet, greased glass, and, when dry, are no more slippery than dry glass. The coatings of the invention are resistant to removal by wet abrasion as determined by running water over the coatings and rubbing between tightly gripped fingers while wet. The inventive coatings have high adherence when dry, as determined by attaching adhesive tape, pulling the tape off with a vigorous action, and then wetting the coated substrate to determine whether the taped portion retained the lubricant coating. The inventive coatings remain adherent and coherent for extended periods when stored in water, and neither peel off, dissolve, nor dissociate.

The coating systems described herein will produce hydrophilic lubricant coatings, resistant to wet abrasion on surfaces such as polyethylene, polypropylene, silicon, glass stainless steel, and other substrates generally considered as presenting adherence problems. It may be necessary to treat such surfaces with gas plasma or other ionizing treatment to promote adhesion to the substrates. The following examples show how the invention can be used.

EXAMPLE 1

Polyurethane tubing was dip coated in a stabilizing polymer solution of
- 5.4 gm low viscosity ½ second nitrocellulose
- 2.0 gm dibutylphthalate
- 1.5 gm camphor
- 1.9 gm polyvinylbutyral in a solvent mixture of
- 36.0 ml toluene
- 13.1 ml butylacetate
- 5.9 ml isopropanol
- 25.4 ml ethylacetate
- 18.1 ml ethanol
- 1.5 ml acetone.

The coated tube was dried for 5 minutes at 65° C. It was then dip coated with a hydrophilic polymer solution containing
- 6.6 gm polyvinylpyrrolidone
- 63.8 ml denatured ethanol
- 23.6 ml ethyl acetate
- 12.6 ml dimethylformamide and dried 5 minutes at 65° C. A hydrophilic coating resulted which was slippery when wet.

EXAMPLE 2

Styrenebutadiene tubing was dip coated in a stabilizing polymer solution containing 1.9 gm ½ second nitrocellulose together with a hydrophilic polymer, 1.5 gm polyvinylpyrrolidone, in
- 60 ml ethylacetate
- 34.4 ml denatured ethanol
- 4.6 ml acetic acid
- 1 ml isopropanol and dried 5 minutes at 80° C. The sample was then dip coated in a hydrophilic polymer solution containing 7.5 gm polyvinylpyrrolidone together with a stabilizing polymer, 0.3 gm nitrocellulose, in
- 73 ml denatured ethanol
- 26.8 ml ethylacetate
- 0.2 ml isopropanol and dried 5 minutes at 80° C. A hydrophilic coating resulted that was lubricious when wet.

EXAMPLE 3

Polyurethane tubing was dip coated with a stabilizing and hydrophilic polymer solution containing 5.9 gm ½ sec. cellulose acetate butyrate and 5.9 gm polyvinylpyrrolidone in 33 ml ethyl acetate and 67 ml chloroform and dried 5 minutes at 80° C. This was then dip coated in a hydrophilic polymer solution containing 5 gm polyvinylpyrrolidone in 95 ml denatured ethanol and dried 5 minutes at 80° C. A hydrophilic coating resulted that was lubricious when wet.

EXAMPLE 4

Samples of polyurethane tubing were coated with a stabilizing and adherent polymer solution containing
- 1.9 gm nitrocellulose
- 1.1 gm polyester resin
- 1.0 gm monobutylester of polymethylvinylether/maleic anhydride copolymer
- 0.8 ml isopropanol
- 57.8 ml ethylacetate
- 33.4 ml denatured ethanol
- 8 ml dimethylformamide.

The sample was dried five minutes at 80° C. The samples were then dip coated in a hydrophilic polymer solution containing
- 6.6 gm polyvinylpyrrolidone
- 63.8 ml denatured ethanol
- 23.6 ml ethylacetate
- 12.6 ml dimethylformamide The sample was dried five minutes at 80° C., to produce an adherent, lubricious, layered coating. A similar coating was also produced on polyvinylchloride tubing.

EXAMPLE 5

This example shows how different "adhesive" resins can be added to promote adhesion to a substrate.

a. The following stabilizing polymer solution was dip coated on polyurethane tubing and dried 5 minutes at 80° C.

| | | |
|---|---|---|
| nitrocellulose | 56 | gm |
| camphor | 15 | gm |
| dibutylphthalate | 20 | gm |
| isopropanol | 23 | ml |
| toluene | 225 | ml |
| ethyl acetate | 330 | ml |
| butyl acetate | 96 | ml |
| acetone | 7 | ml |

This was then dip coated with a hydrophilic polymer solution:

| | | |
|---|---|---|
| polyvinylpyrrolidone (PVP) | 3 | gm |
| denatured ethanol | 27 | ml |
| ethyl acetate | 10 | ml |
| dimethylformamide | 12 | ml |

The coating separated from the tubing when immersed in water.

b. Example 5(a) was repeated with from 5.0 gm to 17 gm of polyurethane resin added to the nitrocellulose solution to produce samples that showed excellent adhesion when immersed in water.

c. Example 5(a) was repeated with from 5.0 gm to 17.0 gm polyester resin added to the nitrocellulose solution to produce samples that showed excellent adhesion when immersed in water.

d. Example 5(a) was repeated with from 5.0 gm to 17.0 gm of styrene butadiene resin added to the nitrocellulose solution to produce samples that showed excellent adhesion when immersed in water.

e. Example 5(a) was repeated with from 5.0 gm to 17.0 gm of urea formaldehyde resin added to the nitrocellulose solution to produce samples that showed excellent adhesion when immersed in water.

EXAMPLE 6

Polyurethane tubing was coated with the following stabilizing polymer solution and dried five (5) minutes at 65° C.

| | | |
|---|---|---|
| nitrocellulose | 65 | gm |
| dibutylphthalate | 24 | gm |
| camphor | 18 | gm |
| polyvinylbutyral | 23 | gm |
| acetone | 28 | ml |
| ethanol | 306 | ml |
| butyl acetate | 257 | ml |
| ethyl acetate | 500 | ml |
| toluene | 550 | ml |
| isopropanol | 28 | ml |

-continued

| | |
|---|---|
| dimethylformamide | 200 ml |

The sample was then overcoated with the following hydrophilic polymer solution and dried five (5) minutes at 65° C.

| | | |
|---|---|---|
| polyvinylpyrrolidone | 1 | gm |
| ethanol | 9 | ml |
| dimethylformamide | 3 | ml |
| water | 0.5 | ml |

This sample had excellent adhesion when immersed in water.

EXAMPLE 7

An acrylic surface was coated with the following stabilizing polymer solution and dried five (5) minutes at 70° C.

| | | |
|---|---|---|
| cellulose acetate propionate | 12.9 | gm |
| dibutylphthalate | 4.8 | gm |
| camphor | 3.6 | gm |
| acetone | 3.2 | gm |
| ethyl acetate | 55.7 | gm |
| toluene | 58.6 | gm |
| butyl acetate | 28.5 | gm |
| isopropanol | 5.6 | gm |

This sample was then coated with the following hydrophilic polymer solution and dried five (5) minutes at 70° C.

| | | |
|---|---|---|
| acetonitrile | 5 | ml |
| ethanol | 4.5 | ml |
| PVP (360,000 mw) | 0.5 | gm |

The coating was not soluble in water and was very slippery.

EXAMPLE 8

An acrylic surface was coated with the following stabilizing polymer solution and dried five (5) minutes at 70° C.

| | | |
|---|---|---|
| cellulose acetate | 12.9 | gm |
| dibutylphthalate | 4.8 | gm |
| camphor | 3.6 | gm |
| methylethylketone | 148.3 | ml |
| dimethylformamide | 20.0 | ml |

The sample was then coated with the following hydrophilic polymer solution and dried five minutes at 70° C.

| | | |
|---|---|---|
| PVP (360,000 mw) | 0.5 | gm |
| cellulose acetate | 0.1 | gm |
| acetone | 6 | ml |
| ethanol | 4.5 | ml |
| acetic acid | 1.0 | ml |
| methylethylketone | 0.9 | gm |

The coating was insoluble in water and was very lubricious.

EXAMPLE 9

An acrylic surface was coated with the following stabilizing and adherent polymer solution and dried five minutes at 70° C.

| | | |
|---|---|---|
| cellulose acetate butyrate | 6.5 | gm |
| polyester resin | 6.0 | gm |
| dibutylphthalate | 2.4 | gm |
| camphor | 1.8 | gm |
| acetone | 2.5 | ml |
| ethyl acetate | 43.6 | ml |
| toluene | 43.6 | ml |
| butylacetate | 22.4 | ml |

The sample was then coated with the following hydrophilic polymer solution and dried five (5) minutes at 70° C.

| | | |
|---|---|---|
| acetonitrile | 5 | ml |
| ethanol | 4.5 | ml |
| PVP (360,000 mw) | 0.5 | gm |

This coating was water insoluble and was lubricious when wet.

EXAMPLE 10

Nylon tubing was coated with stabilizing polymer with the following solution and dried ten (10) minutes at 75° C.

| | | |
|---|---|---|
| nylon resin | 2 | gm |
| trifluoroethanol | 18 | ml |

The sample was then overcoated with hydrophilic polymer with the following solution and dried ten (10) minutes at 75° C.

| | | |
|---|---|---|
| PVP (360,000 mw) | 1.0 | gm |
| nylon resin | 0.3 | gm |
| ethanol | 9.0 | ml |
| dimethylformamide | 3.0 | ml |
| trifluoroethanol | 2.7 | ml |

This coating was not water soluble.

EXAMPLE 11

A stainless steel wire guide was coated with stabilizing polymer with the following solution and dried ten minutes at 70° C.

| | | |
|---|---|---|
| nitrocellulose | 64.6 | gm |
| dibutylphthalate | 24.3 | gm |
| camphor | 17.9 | gm |
| polyvinylbutyral | 22.5 | gm |
| acetone | 28.4 | ml |
| ethanol | 306.1 | ml |
| butylacetate | 257.0 | ml |
| ethylacetate | 499.2 | ml |
| toluene | 552.8 | ml |
| isopropanol | 27.5 | ml |
| dimethylformamide | 200.0 | ml |

The sample was then overcoated with hydrophilic polymer with the following solution and dried ten (10) minutes at 70° C.

| | |
|---|---|
| PVP | 1.0 gm |
| ethanol | 9.0 ml |
| dimethylformamide | 2.0 ml |

This coating was insoluble in water and was very lubricious.

EXAMPLE 12

The coating method of example 11 was repeated on an acrylic surface and also produced a coating that was insoluble in water and very lubricious.

EXAMPLE 13

Nylon tubing was coated with a stabilizing and adherent polymer with the following solution and dried for five (5) minutes at 65° C.

| | |
|---|---|
| nitrocellulose | 32.3 gm |
| polyurethane | 11.2 gm |
| dibutylphthalate | 12.2 gm |
| camphor | 9.0 gm |
| polyvinylbutyral | 11.2 gm |
| acetone | 25 ml |
| ethanol | 254 ml |
| butylacetate | 225.3 ml |
| ethylacetate | 439.2 ml |
| toluene | 467.8 ml |
| isopropanol | 13.8 ml |
| dimethylformamide | 100 ml |

The sample was then coated with hydrophilic polymer with the following solution and dried five (5) minutes at 65° C.

| | |
|---|---|
| PVP | 1.0 gm |
| nitrocellulose | 0.12 gm |
| ethanol | 9.0 ml |
| dimethylformamide | 3.0 ml |
| ethylacetate | 0.4 ml |

This coating was insoluble in water and was very lubricious.

EXAMPLE 14

Polyurethane tubing was coated with the following stabilizing polymer solution and dried five (5) minutes at 65° C.

| | |
|---|---|
| nitrocellulose | 64.6 gm |
| dibutylphthalate | 24.3 gm |
| camphor | 17.9 gm |
| polyvinylbutyral | 22.5 gm |
| acetone | 28.4 ml |
| ethanol | 306.1 ml |
| butylacetate | 257.0 ml |
| ethylacetate | 449.2 ml |
| toluene | 552.8 ml |
| isopropanol | 27.5 ml |
| dimethylformamide | 200.0 ml |

This sample was then overcoated with the following hydrophilic polymer solution and dried five minutes at 65° C.

| | |
|---|---|
| PVP | 1.0 gm |
| ethanol | 9.0 ml |
| dimethylformamide | 2.0 ml |

This sample coating was insoluble in water and very lubricious when wet.

EXAMPLE 15

Polyvinylchloride tubing was treated in the same way as the nylon tubing in example 13. The resulting coating was insoluble and very lubricious.

EXAMPLE 16

A sample of styrene-butadiene tubing was coated with stabilizing and adherent polymer with the following solution and dried five (5) minutes at 80° C.

| | |
|---|---|
| nitrocellulose | 32.3 gm |
| polyurethane | 10.0 gm |
| dibutylphthalate | 12.2 gm |
| camphor | 9.0 gm |
| polyvinylbutyral | 11.2 gm |
| acetone | 25 ml |
| ethanol | 264 ml |
| butylacetate | 226.3 ml |
| ethyl acetate | 439.2 ml |
| toluene | 467.8 ml |
| isopropanol | 13.8 ml |
| dimethyformamide | 100 ml |

The sample was then coated with the following hydrophilic polymer solution and dried five minutes at 80° C.

| | |
|---|---|
| PVP | 1.0 gm |
| ethanol | 9.0 ml |
| dimethylformamide | 3.0 ml |
| water | 0.5 ml |

This sample was insoluble in water and was lubricious when wet.

EXAMPLE 17

This example shows how solvent(s) can be added which improves adhesion by etching or interacting with the layer onto which it is being coated. Several samples of polyurethane tubing were coated with the following stabilizing polymer solution.

| | |
|---|---|
| nitrocellulose | 64.6 gm |
| dibutylphthalate | 24.3 gm |
| camphor | 17.9 gm |
| polyvinylbutyral | 22.5 gm |
| acetone | 28.4 ml |
| ethanol | 306.1 ml |
| butylacetate | 257.0 ml |
| ethyl acetate | 499.2 ml |
| toluene | 552.8 ml |
| isopropanol | 27.5 ml |
| dimethylformamide | 200.0 ml |

Samples coated as above were then coated with one of the following solutions containing various amounts of dimethylformamide or acetic acid, which interact with the surface being coated in order to promote adhesion:
(a) Coat with the following hydrophilic polymer solution and dry five (5) minutes at 70° C.

| | |
|---|---|
| PVP | 1.0 gm |

-continued

| | |
|---|---|
| ethanol | 9.0 ml |
| dimethylformamide | 3.0 ml |

This hydrophilic coating adhered well, was insoluble in water, and was very lubricious.

(b) Coat with hydrophilic polymer, 10% (w/v) PVP in ethanol and dry five (5) minutes at 70° C. This hydrophilic coating dissolved in water and came off.

(c) Coat with the following hydrophilic polymer solution and dry five (5) minutes at 70° C.

| | |
|---|---|
| PVP | 1.0 gm |
| ethanol | 9.0 ml |
| dimethylformamide | 1.0 ml |

This sample resisted removal when wet, but was not as resistant to wet abrasion as the sample above containing three (3) ml of dimethylformamide.

(d) Coat with the following hydrophilic polymer solution and dry five (5) minutes at 70° C.

| | |
|---|---|
| PVP | 1.0 gm |
| ethanol | 9.0 ml |
| acetic acid | 3.0 ml |

This hydrophilic coating adhered well, was insoluble in water, and was very lubricious.

EXAMPLE 18

In this example, the hydrophilic polymer and the stabilizing polymer were combined into a single solution, which was coated on polyurethane tubing and dried five (5) minutes at 80° C.:

| | |
|---|---|
| PVP | 0.5 gm |
| nitrocellulose | 0.056 gm |
| methylethylketone | 13.7 ml |
| isopropanol | 0.024 gm |
| acetic acid | 1.0 ml |

This produced a single-layer coating that was lubricious when wet and was resistant to wet abrasion.

I claim:

1. A lubricious composite, comprising
an outer layer having an exposed outer surface, said outer layer comprising a hydrophilic polymer selected from the group consisting of polyvinylpyrollidone, polyvinylpyrollidone-polyvinyl acetate copolymer, a mixture of the above, and the like,
an inner layer comprising a water-insoluble stabilizing polymer selected from the group consisting of a cellulose ester, a copolymer of polymethyl vinyl ether and maleic anhydride, an ester of the copolymer, and nylon,
said composite being substantially more slippery when wet than when dry, resistant to removal by wet abrasion, and essentially insoluble in aqueous solution, the ratio of said hydrophilic polymer to said stabilizing polymer altering the degree of wet lubricity, resistance to removal, and insolubility of said composite.

2. The coating of claim 1, wherein said inner layer includes a hydrophilic polymer.

3. The coating of claim 1, wherein said outer layer includes a stabilizing polymer.

4. The coating of claim 1 which is applied to a metallic substrate.

5. The coating of claim 1 which is applied to glass.

6. The coating of claim 1 which is applied to a polymeric substrate selected from the group consisting of polyurethane, polyvinylchloride, polyacrylate, polycarbonate, polystryrene, polyester resins, polybutadiene-styrene copolymers, nylon, polypropylene, polybutylene, teflon, silicon, and polyvinyl acetal.

7. An article having a lubricious composite coating, comprising
an outer layer having an exposed outer surface, said outer layer comprising a hydrophilic polymer selected from the group consisting of polyvinylpyrollidone, polyvinylpyrollidone-polyvinyl acetate copolymer; a mixture of the above, and the like,
an inner layer comprising a water-insoluble stabilizing polymer selected from the group consisting of a cellulose ester, a copolymer of polymethyl vinyl ether and maleic anhydride, an ester of the copolymer, and nylon,
a substrate to which said inner layer adheres,
said composite being substantially more slippery when wet than when dry, resistant to removal by wet abrasion, and essentially insoluble in aqueous solution, the ratio of said hydrophilic polymer to said stabilizing polymer altering the degree of wet lubricity, resistance to removal, and insolubility of said composite.

8. The article of claim 7, wherein said hydrophilic polymer is selected from the group consisting of polyvinylpyrrolidone and polyvinylpyrrolidone-vinyl acetate, and said stabilizing polymer is selected from the group consisting of cellulose acetate, cellulose acetate butyrate, cellulose acetate proprionate, cellulose nitrate, ethyl cellulose, and hydroxyethyl cellulose.

9. The article of claim 8, wherein said inner layer includes a plasticizing agent.

10. The article of claim 8, wherein said inner layer includes an adherent polymer for promoting bonding between said substrate and said inner layer.

11. The article of claim 7, wherein said substrate is metal.

12. The article of claim 7, wherein said substrate is glass.

13. The article of claim 7, wherein said substrate is selected from the group consisting of polyurethane, polyvinylchloride, polyacrylate, polycarbonate, polystryrene, polyester resins, polybutadiene-styrene copolymers, nylon, polypropylene, polybutylene, teflon, silicon, and polyvinyl acetal.

14. The coating of claim 1 in which the stabilizing polymer is selected from the group consisting of cellulose acetate, cellulose acetate butyrate, cellulose acetate proprionate, cellulose nitrate, ethyl cellulose, and hydroxyethyl cellulose.

15. The coating of claim 1 which further comprising an adherent polymer.

16. The coating of claim 1, further comprising an adherent polymer selected from the group consisting of polyester, polyurethane, styrene polybutadiene, acrylic resin, polyvinylidene chloride, polycarbonate, and polyvinylchloride, 17. The coating of claim 1, further comprising a plasticizing agent.

18. The coating of claim 1, further comprising a plasticizing agent selected from the group consisting of camphor, polyvinyl butyral, dibutylphthalate, castor oil, dioctyl phthalate, acetyl tributyl citrate, dibutyl sebacate, sebacic acid, and alkyl resin.

* * * * *